(12) United States Patent
Meley

(10) Patent No.: US 9,629,695 B2
(45) Date of Patent: Apr. 25, 2017

(54) ORTHODONTIC WORKING ANATOMIC ARCH, AND ORTHODONTIC TREATMENT SYSTEM INCLUDING ANATOMIC WIRE

(76) Inventor: Antoine Meley, Epernon (FR)

( * ) Notice: Subject to any disclaimer, the term of this patent is extended or adjusted under 35 U.S.C. 154(b) by 223 days.

(21) Appl. No.: 13/497,792

(22) PCT Filed: Sep. 24, 2010

(86) PCT No.: PCT/EP2010/064141
§ 371 (c)(1),
(2), (4) Date: Jul. 9, 2012

(87) PCT Pub. No.: WO2011/036249
PCT Pub. Date: Mar. 31, 2011

(65) Prior Publication Data
US 2012/0270174 A1    Oct. 25, 2012

(30) Foreign Application Priority Data
Sep. 25, 2009  (FR) ..................... 09 56657

(51) Int. Cl.
| A61C 3/00 | (2006.01) |
| A61C 7/12 | (2006.01) |
| A61C 7/14 | (2006.01) |
| A61C 7/20 | (2006.01) |
| A61C 7/28 | (2006.01) |

(52) U.S. Cl.
CPC ................. *A61C 7/12* (2013.01); *A61C 7/145* (2013.01); *A61C 7/20* (2013.01); *A61C 7/28* (2013.01)

(58) Field of Classification Search
CPC .... A61C 7/08; A61C 7/10; A61C 7/12; A61C 7/125; A61C 7/14; A61C 7/141; A61C 7/143; A61C 7/145; A61C 7/146; A61C 7/148; A61C 7/16; A61C 7/18; A61C 7/20; A61C 7/22; A61C 7/28; A61C 7/282; A61C 7/285; A61C 7/287; A61C 7/30; A61C 7/303; A61C 7/34; A61C 7/36
USPC ........................................ 433/6–24
See application file for complete search history.

(56) References Cited

U.S. PATENT DOCUMENTS

| 3,052,028 A | 9/1962 | Wallshein | |
| 5,310,340 A * | 5/1994 | Zedda ............... | 433/8 |
| 5,823,771 A | 10/1998 | Nord | |
| 7,121,825 B2 * | 10/2006 | Chishti et al. ...... | 433/6 |
| 2004/0067463 A1* | 4/2004 | Rosenberg ......... | 433/6 |

(Continued)

FOREIGN PATENT DOCUMENTS

| DE | 10 2005 024 587 | 11/2006 |
| EP | 0 551 800 A1 | 7/1993 |
| JP | 2005 110830 | 4/2005 |

*Primary Examiner* — Yogesh Patel
(74) *Attorney, Agent, or Firm* — Blakely Sokoloff Taylor & Zafman LLP

(57) ABSTRACT

The invention relates to an orthodontic working arch wire (2) for moving at least one tooth of a dental arch of patient to be treated from a first spatial configuration toward a second spatial configuration, including an element for connecting (42) to the tooth to be treated, which is intended to be attached onto the tooth being treated by snap-fining onto a bracket glued onto one of the surfaces of said tooth, the working arch wire being rigid, the connecting element being movable relative to the orthodontic working arch wire and connected to the orthodontic working arch wire by elastically deformable connecting means (43, 43a).

11 Claims, 4 Drawing Sheets

(56) References Cited

U.S. PATENT DOCUMENTS

| | | | |
|---|---|---|---|
| 2005/0100853 A1* | 5/2005 | Tadros et al. | 433/6 |
| 2005/0277084 A1* | 12/2005 | Cinader et al. | 433/20 |
| 2006/0177789 A1* | 8/2006 | O'Bryan | 433/6 |
| 2006/0223022 A1* | 10/2006 | Solomon | 433/6 |
| 2007/0065768 A1* | 3/2007 | Nadav | 433/6 |
| 2007/0134611 A1* | 6/2007 | Nicholson | A61C 7/30 433/11 |
| 2007/0184398 A1 | 8/2007 | Cronauer | |
| 2007/0231768 A1* | 10/2007 | Hutchinson | A61C 7/12 433/24 |
| 2008/0233529 A1* | 9/2008 | Kuo et al. | 433/6 |
| 2009/0291406 A1* | 11/2009 | Namiranian et al. | 433/24 |
| 2011/0027743 A1* | 2/2011 | Cinader et al. | 433/11 |
| 2011/0311935 A1* | 12/2011 | Dumas | A61C 7/14 433/16 |

\* cited by examiner

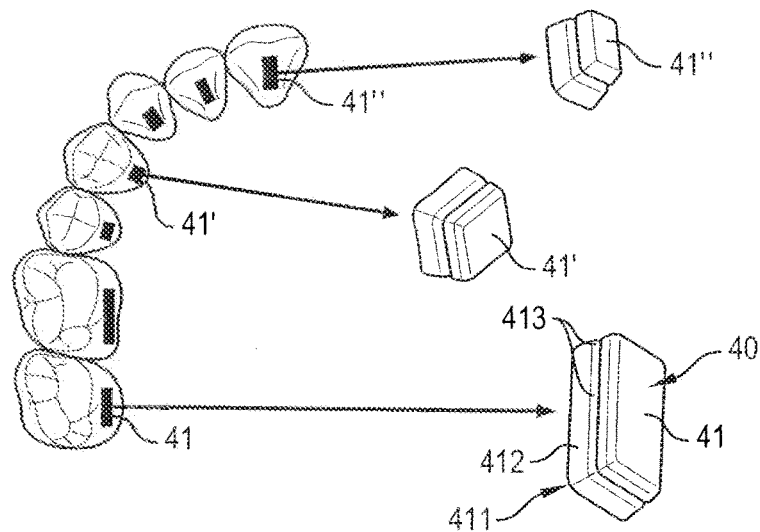
FIG. 4
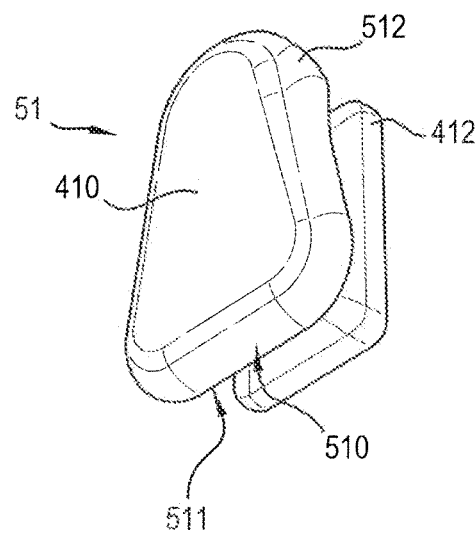
FIG. 4bis

FIG. 5bis

ORTHODONTIC WORKING ANATOMIC ARCH, AND ORTHODONTIC TREATMENT SYSTEM INCLUDING ANATOMIC WIRE

This is a non-provisional application claiming the benefit of International Application Number PCT/EP2010/064141 filed Sep. 24, 2010.

The invention relates to a working arch wire designed for orthodontic correction and anatomically made to measure. The invention also relates to an orthodontic treatment system including a series of these orthodontic working arch wires.

Orthodontic treatment systems allow the correction of the position of a certain number of teeth located on the dental arches of the maxilla and/or the mandible of a patient. To this end, orthodontic treatment systems comprise collapsible metal arches, force generators attached onto the connectors, which are themselves attached onto the teeth to be moved or to be used as abutments. These applied forces are tension/compression and/or torsion forces. The metal arches are placed on the dental arches either vestibularly or lingually. The forces are transmitted to the teeth to be moved through connectors glued to them. In current devices, the metal arches which rest on other teeth, involved or not in the treatment, consequently generate parasitic forces on the latter teeth in reaction to the forces thus generated. One of the difficulties in orthodontic practice is how best to control, during the patient's treatment, these parasitic reaction forces which reduce the effectiveness of the treatment, in order to attain an optimal treatment.

For example, document US 2004/0048223 describes an orthodontic treatment system consisting of transmitting forces on the teeth to be treated by maxillary and/or mandibular caps made of semirigid material, covering the occlusal faces of all the teeth of the dental arch. The forces exerted on the teeth to be treated are obtained by an offset between the shape of the caps and stops attached onto the teeth to be treated. However, in this system the forces are not completely individualized and parasitic reaction forces are exerted on the teeth adjacent to the teeth to be treated.

In document US 2006/0099544, the orthodontic treatment system described includes an elastomer arch having recesses for receiving specific hooks or brackets glued to the teeth. However, in this second system, the resilience of this arch, though allowing the movement of the teeth to be treated, does not make it possible to decouple movements and, consequently, to individualize the forces to only the teeth to be treated. Once again parasitic reaction forces are exerted on the teeth adjacent to the teeth to be treated.

Also, these two methods alter interdental relationships by emplacing non-conformal, harmful and uncomfortable occlusal contacts.

One goal of the invention is to provide an orthodontic treatment system including orthodontic working wire arches which minimize parasitic reaction forces due to the forces needed for treating a tooth to be moved.

To this end there is provided, according to the invention, an orthodontic working wire arch designed to move at least one tooth to be treated in the dental arch of a patient from a first spatial configuration toward a second spatial configuration, the arch including an element for connecting to the tooth to be treated, attached onto said tooth to be treated, the working wire arch being rigid, the connecting element being movable with respect to the orthodontic working wire arch by elastically deformable connecting means.

Thus, the use of a connecting element that is movable with respect to the working wire arch makes it possible to optimally individualize the forces designed to move the tooth to be treated between two spatial configurations, the parasitic reaction forces being absorbed by the rigid orthodontic working wire arch by being distributed over the totality of this working wire arch.

Advantageously, but optionally, the orthodontic working wire arch has at least one of the following additional features:

the connecting element includes a connector designed to be attached onto the tooth to be treated;
the connecting element includes a connecting base connected to the orthodontic working wire arch by elastically deformable connecting means;
The connecting base includes a recess designed to receive the connector;
The connector is inserted into the recess by clip action or by a vertical forked tenon;
the recess has a shape complementary to a shape of the connector;
the connector has the general shape of a truncated pyramid, particularly individualized in its shape and dimensions;
the connector has, ringing it, a sunken groove or a bead in relief;
the connector consists of three portions arranged so as to form a stress breaker of the silentbloc type;
the orthodontic working arch wire also has a cavity designed to receive all or part of the connecting element;
the elastically deformable connecting means are of the same material as the orthodontic working wire arch and part of the connecting element, so that there is no discontinuity of material between the orthodontic working wire arch and the part of the connecting element;
the connecting means include at least one tab and/or an alveolar structure and/or a pontic connection;
the orthodontic working wire arch includes a metal web designed to generate a force tending to open and/or to close the orthodontic working wire arch by spring effect;
the orthodontic working wire arch includes a channel designed to receive a metal web;
the working wire arch includes one or more extensions covering the gum allowing remote anchorage, particularly by clipping, onto a screw threaded into the bone;
the working wire arch is so arranged as not to disturb the inter-arch relationships by not covering the occlusal surfaces of the teeth; and
the working wire arch is made of plastic, such as PA12 or PA6-6 polyamide.

There is also provided, according to the invention, an orthodontic treatment system designed to carry out a displacement of at least one tooth to be treated in a dental arch of a patient from an initial spatial configuration toward a desired final spatial configuration, comprising a series of orthodontic working wire arches having at least one of the foregoing features, so as to carry out the displacement by successive steps, each orthodontic working wire arch carrying out one step.

Other features and advantages of the invention will appear from the following description of a preferred embodiment of the invention. In the appended drawings:

FIG. 4 is a half-elevation at the occlusal faces of a dental arch illustrating different connector forms of an orthodontic working wire arch according to the invention;

FIG. 4bis is a three-dimensional view of a variation of implementation of a connector of an orthodontic working wire arch according to the invention;

FIGS. 5 and 5bis are front and back partial exploded views of a connecting base of an orthodontic working wire arch according to the invention;

Figure 1:
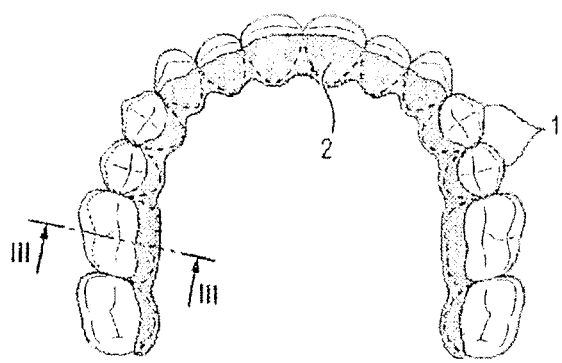
FIG. 1 is a view of the occlusal surface of a dental arch equipped lingually with an orthodontic working wire arch according to the invention.
Figure 2:
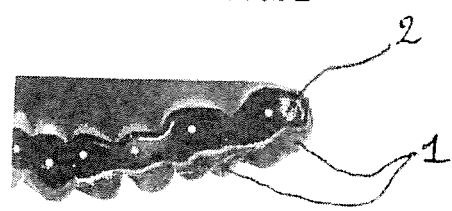
FIG. 2 is a partial three-dimensional isometric view of FIG. 1.

With reference to FIGS. 1 and 2, an orthodontic working wire arch 2 according to the invention is made to measure and anatomically to be positioned on the lingual or vestibular faces of the teeth of a dental arch 1. Here, in FIGS. 1 and 2, the orthodontic working wire arch is positioned on the lingual faces of the teeth of the dental arch 1. The lingual or vestibular faces of the teeth 1 are totally or partially covered by the orthodontic working wire arch 2. This arrangement makes it possible to not cover the occlusal grinding surfaces of the teeth of the dental arch whereon is placed the orthodontic working wire arch 2 according to the invention.

Figure 3:
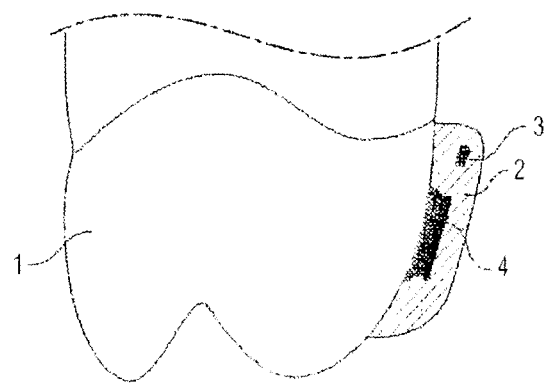
FIG. 3 is a section view along line of the orthodontic working wire arch of FIG. 1 mounted on a tooth.

With reference to FIG. 3, we will describe generally the attachment to a tooth 1 of an orthodontic working wire arch 2 according to the invention. On the surface, here the lingual surface, of the tooth 1 is glued a connecting element 4, or even a connector, to which is connected the orthodontic working wire arch 2, by clipping for example. In section, the orthodontic working wire arch 2 according to the invention has a section shape one profile whereof substantially follows the surface of the tooth whereon the orthodontic working wire arch 2 according to the invention is designed to be positioned. In the implementation variation illustrated here in FIG. 3, the orthodontic working wire arch 2 according to the invention includes a reinforcing web 3. This reinforcing web 3 makes it possible to increase the corrective actions of the orthodontic working wire arch 2 according to the invention in remodeling the overall shape of the dental arch whereon is installed the orthodontic working wire arch according to the invention.

Generally, the orthodontic wire arch 2 is made of plastic compatible with use in the mouth. Considering the stresses required to exert the correction forces on the teeth, on the one hand, and on the other hand to carry out the remodeling of the dental arch whereon the orthodontic working wire arch 2 is installed, the material must have specific compressive, tensile and flexural strength characteristics. In particular, the material used is a PA 12 polyamide or possibly a PA6-6 polyamide. For its part, the reinforcing web 3 is generally a metal wire making it possible, by spring effect, to open or to close the orthodontic working wire arch 2 wherein it is installed. As is known per se, the metal wire forming the reinforcing web 3 is made of titanium.

Now, with reference to FIG. 4, we will describe the connectors 41, 41', 41" making it possible to attach an orthodontic working wire arch 2 according to the invention. To each of the surfaces, lingual surfaces here, of the teeth 1 of the dental arch to be corrected is bonded a connector 41, 41', 41". These connectors 41, 41', 41" are generally of truncated pyramidal shape, with a substantially rectangular or substantially triangular base, or of a conical parallelopipedal shape each having a base 411 whereon is applied an suitable adhesive in order to glue the connector onto one of the vestibular and lingual surfaces of the tooth 1. Each of the connectors 41, 41', 41" has an upper face 410 spaced substantially parallel to the base 411. The base 411 and the upper face 410 are of generally rectangular shape, the upper face 410 being homothetically smaller with respect to the base 411. Connecting on each of the sides the base 411 with the upper face 410, each of the connectors 41, 41', 41" has lateral faces 412 sloping toward each other. The faces 412 have a sunken groove 413 which forms here a continuous or discontinuous ring on the connectors 41, 41', 41". As a variation of implementation, the faces 412 have a bead in relief instead and in the place of the foregoing groove 413. The dimensions of the base 411, and consequently of the upper face 410, are matched to the lingual or vestibular surface of the tooth 1 whereon said base 411 is designed to be bonded. This makes it possible to optimize and to ensure, on the one hand, the adhesion of the connector on the tooth throughout the entire treatment of the patient and, on the other hand, the transmission of forces which are likely to be necessary for a desired displacement of the tooth to be treated.

With reference to FIG. 4b is, the connector 51 has a base 411 to which is applied a suitable adhesive in order to glue the connector to one of the vestibular and lingual faces of the tooth. Here, this base is of substantially rectangular shape. It is topped with a narrowed neck 511 on which is laid a head 512. The head 512 includes an upper face 410 and a bead 510 in relief extending belt-wise along a lateral boundary of said head 512. The head has a substantially triangular shape, the corners whereof are rounded. This rounded shape makes it possible to avoid causing injuries.

As a variation of implementation, connectors of the silentbloc type can be made up of three irreversibly assembled portions comprising: a base whereon is applied an appropriate adhesive in order to glue the connector onto one of the vestibular and lingual surfaces of the tooth 1, this base being topped with a force transmitting structure, capped with an elastic polymer of the rubbery or polyurethane, or even silicone type, and the assembly finally being wrapped in a carcase, the development of an outer face whereof is similar to an outer face of the connectors previously described.

Figure 5:
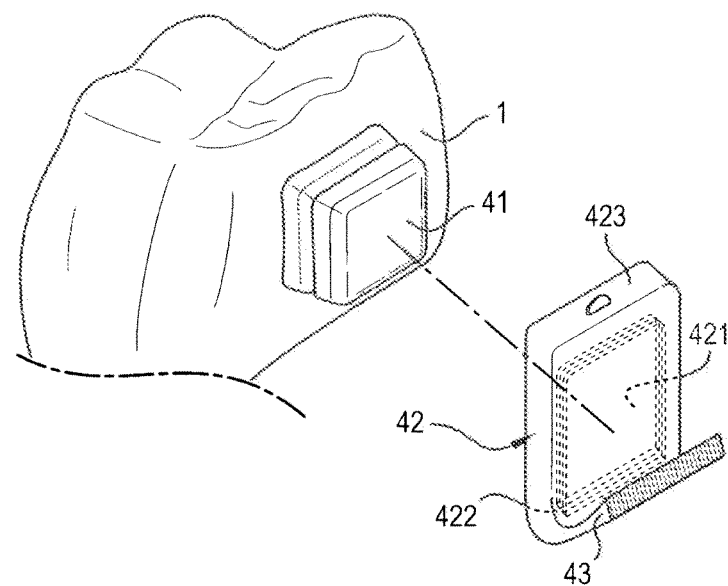
Figure 5:
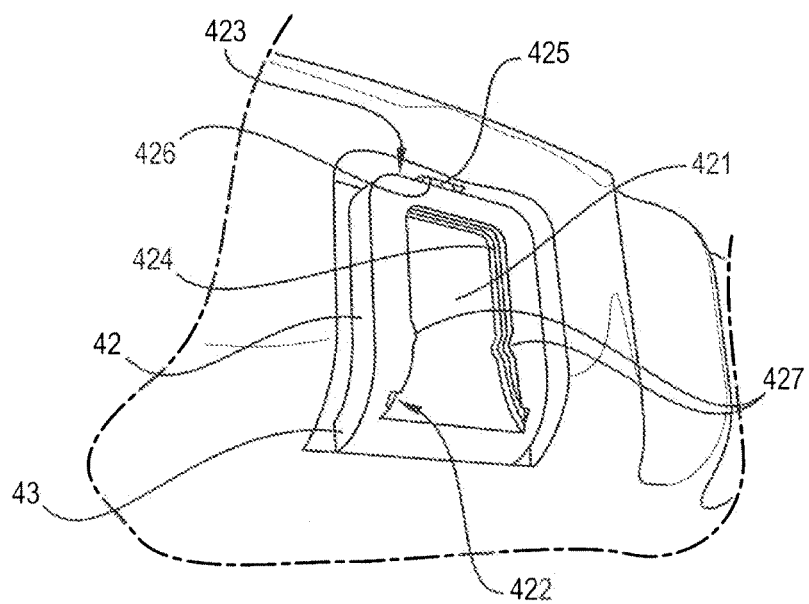

With reference to FIG. 5, will describe in detail a connecting element 4 between the tooth 1 and the orthodontic working wire arch 2 according to the invention, which makes it possible to individually straighten or move said tooth between a first spatial configuration and a second spatial configuration, once the orthodontic working wire arch is positioned in the patient's mouth. To that end, the connecting element 4 has, in addition to a connector 41 attached onto the lingual or vestibular surface of the tooth 1 to be treated, a connecting base 42 connected to the orthodontic working wire arch 2 according to the invention by elastically deformable connecting means 43. The connecting base 42 is of generally paralellopipedal shape and includes a cavity 421 extending as a hollow into one face of the connecting base 42 designed to be facing the connector 41 when the orthodontic working wire arch 2 according to the invention is mounted to the tooth 1. The shape of the cavity 421 is the complement of the shape of the connector 41 so that the cavity 421 receives, during said assembly, the connector 41 clip action or clipping.

As a variation of implementation illustrated in FIG. 5b is, a lug 425 located on the face 423 opposite the connecting base makes it possible to limit the movement of the tab by cooperation with a hollow receptacle 426 located facing it in the working wire arch 1.

When the connector 41 is clipped into the cavity 421, the cavity 421 has a protuberance 424 (alternately a depression) extending in relief (alternately in depression) from at least one lateral face of the cavity 421 toward the inside thereof and designed to be received in the groove 413 (alternately, to receive the bead in relief) of the connector 41. As a variation in implementation the protuberance (424) extends belt-wise over all or part of a periphery of the cavity 421.

In another variation of implementation, the connecting base 42 includes, from an upper lateral face 423, a groove 422 opening into the cavity 421. Such a vertical groove 422 makes it possible to assemble the connecting base 42 by a forked tenon joint to the connector 41 attached onto the tooth 1 upon upward or downward vertical motion, depending on whether the orthodontic working wire arch 2 is mounted on the maxilla or on the mandible of the patient. One or two boss retainers 427 make it possible to hold the connecting base firmly to the connector 41 by resisting tearout or unclipping forces, by constituting an undercut in the engagement direction.

Figure 6:
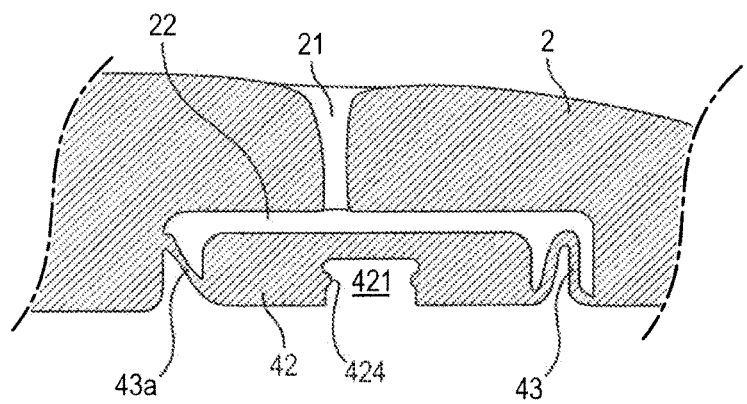
FIG. 6 is a partial section view showing the arrangement between the orthodontic working wire arch according to the invention and a connecting base; and, FIGS. 7a through 7c illustrate different connections between the orthodontic working wire arch according to the invention and the connecting base.
Figure 7:
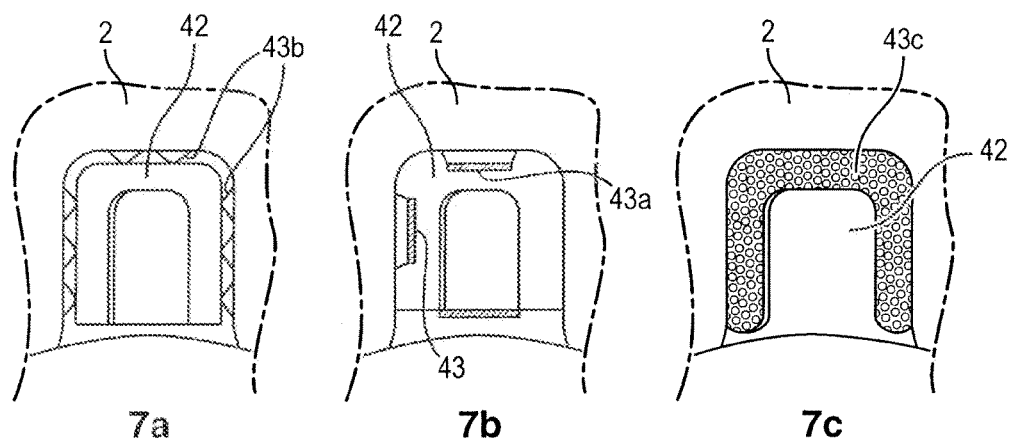

With reference to FIG. 6 and FIG. 7, we will describe in greater detail the interaction between the connecting base 42 and the orthodontic working wire arch 2 according to the invention. Facing the working base 42, the orthodontic working wire arch 2 has a cavity 22 as well as an opening 21 running through a thickness of the orthodontic working wire arch 2 from the bottom of the cavity 22 to one opposite face of the orthodontic working wire arch 2. This opening 21 has two advantages:

it makes it possible to press on the connecting base using an instrument capable of passing through it, in order to correctly clip the working wire arch onto the connectors in difficult locations, and
  it allows movement of fluids, saliva among others, to and out of the cavity 22 during a displacement of the connecting base 42 within this cavity 22 of the orthodontic working wire arch 2 according to the invention.

Here, illustrated in FIG. 6, the connecting base 42 is connected to the working wire arch 2 by elastically deformable connecting means 43, 43a which are shown here as tabs. The shapes of the tabs constituting the elastically deformable connecting means 43, 43a are diverse and varied and especially suited by their shape to the spatial displacement of the tooth 1 to be treated to move from a first spatial configuration to a second spatial configuration by a translation movement and/or a rotation movement. In addition to their varied shapes, the number of tabs constituting the elastically deformable connecting means 43, 43a can vary between one and four (each lateral face of the connecting base 42 has one or no tab), which makes it possible to increase the possible displacements that can be performed on the tooth to which the connecting base 42 will be bonded. As a variation of implementation, the elastically deformable connecting means 43, 43a have a narrow pontic connection spread over all or part of a periphery of the connecting base 42 as illustrated in FIG. 7a. In another variation of implementation, the elastically deformable connecting means include a sponge type alveolar structure distributed over all or part of a periphery of the connecting base 42 as illustrated in FIG. 7c. Other structures of elastically deformable connecting means 43 are possible.

Whatever the structure of the elastically deformable connecting means 43, the orthodontic working wire arch 2 according to the invention, the elastically deformable connecting means 43 and the connecting base 42 are made of the same material. This prevents discontinuities of material between the orthodontic wire arch and the connecting base, which would weaken and complicate the orthodontic working wire arch 2 according to the invention.

Such an assembly of the different connecting bases 42 and the orthodontic working wire arch 2 according to the invention allows each of the connecting bases 42 to be able to move within the corresponding cavity 22 of the orthodontic working wire arch 2. The elastically deformable connecting means 43 connecting the connecting base 42 with the orthodontic working wire arch 2 according to the invention make it possible to generate forces transmitted to the tooth to be treated in order to achieve the desired displacement between a first spatial configuration of this tooth and a second desired spatial configuration of this same tooth. Indeed, any movement of the connecting base 42 in the associated cavity 22 of the orthodontic working wire arch 2 gives rise to a force due to the elasticity of the material making up the elastically deformable connecting means. The intensity of this force transmitted by the connecting base 42 to the tooth 1 to be treated therefore depends on the size and on the shape of the structure of the elastically deformable connecting means used on said base 42 connecting to the orthodontic working wire arch 2 according to the invention, a structure that can be modulated as described previously in its manufacture according to the forces to be produced while respecting the physiology of living tissues. This makes it possible to personalize the forces to be produced on each tooth to be treated both in direction, in intensity, and in the movement boundary. Due to its stiffness, the working wire arch allows the parasitic reaction force to the force exerted on the tooth to be treated to be "diluted" in order not to transmit this parasitic force to the teeth adjacent to the teeth to be treated, but to spread it over the entire orthodontic working wire arch, making the parasitic force resulting from this spreading negligible and thus resolving the disadvantage of the current conventional systems. This stiffness of the orthodontic working wire arch allows the latter, once in place on the dental arch to be treated, to retain its shape in reaction to the force exerted on the tooth to be treated. Thus, by not deforming as a result of this reaction, the orthodontic working wire arch allows a spreading of the parasitic reaction force over the entirety of said orthodontic working wire arch.

However, the design of an orthodontic working wire arch 2 according to the invention does not allow transmission of substantially constant forces during dental displacement over distances greater than a few tenths of a millimeter. That is why the orthodontic working wire arches according to the invention must change during the progression of the treatment that allows the displacement of the teeth to be treated between an initial spatial configuration toward a desired final spatial configuration. The successive orthodontic working wire arches comprised in an orthodontic treatment system according to the invention are different from one another and each corresponds to a step in the progression of the desired orthodontic correction of the patient.

We will now briefly describe a method for making an orthodontic working wire arch according to the invention. To this end, an initial step of three-dimensional entry of the configuration of the teeth as well as of their roots of a patient to be treated is carried out by means of an X-ray scanner or a three-dimensional photo scanner (or other frequency spectrum usable for this purpose). Then, based on this data entry, a representation of the arches is integrated and processed in order to allow repositioning of the teeth according to the treatment objectives demanded and desired by the practitioner. A gradual repositioning of the teeth allows the corrected arches to be visualized. This repositioning takes into account the consistency of occlusal relationships during the course of the treatment. A segmentation of this progressive repositioning is then defined, each segment representing a step with which will be associated an orthodontic working wire arch according to the invention. From there, the orthodontic working wire arches according to the invention will be defined, then manufactured on a machine using a so-called laser fusion or stereolithography technique based on data representing the segmentation of the gradual repositioning defined previously. The series of orthodontic working wire arches thus obtained is incorporated into the orthodontic treatment system.

Of course, it is possible to apply numerous modifications to the invention without departing from its scope.

The invention claimed is:

1. An orthodontic assembly comprising
a tooth connector configured to be attached onto a tooth to be treated in a patient's dental arch
a connecting base and a orthodontic working wire arch, wherein
the connecting base includes a cavity configured to receive the tooth connector by vertical engagement of the base into the cavity,
the connecting base includes a boss retainer constituting an undercut for the vertical engagement to hold the connecting base firmly to the tooth connector,
the connecting base is movable with respect to the orthodontic working wire arch and,
the connecting base is connected to the orthodontic working wire arch by elastically deformable connectors, said elastically deformable connectors configured to generate forces transmitted to the teeth to achieve displacement between a first spatial configuration towards a second spatial configuration,
wherein the working wire arch is rigid, and retains its shape in reaction to the force exerted, and prevents parasitic forces from being transmitted to adjacent teeth, wherein the orthodontic working wire arch also includes a cavity designed to receive all or part of the connecting base.

2. An orthodontic assembly according to claim 1, wherein the cavity has a shape that is complementary to that of the tooth connector.

3. An orthodontic assembly according to claim 1, wherein the tooth connector has a generally truncated pyramidal shape.

4. An orthodontic assembly according to claim 1, wherein the elastically deformable connectors are of the same material as the orthodontic working wire arch and part of the connecting base, so that there is no discontinuity of material between the orthodontic working wire arch and the part of the connecting base.

5. An orthodontic assembly according to claim 4, wherein the elastically deformable connectors include at least one tab.

6. An orthodontic assembly according to claim 1, wherein the orthodontic working wire arch is made of plastic.

7. An orthodontic treatment system, designed to carry out the movement of at least one tooth to be treated from an initial spatial configuration toward a desired final spatial configuration, wherein the orthodontic treatment system includes a series of orthodontic assemblies according to claim 1, so as to accomplish the movement by successive steps, each orthodontic working wire arch of the series carrying out one step.

8. An orthodontic assembly according to claim 1, comprising a plurality of said tooth connectors and a plurality of said connecting bases, wherein
the connecting bases are connected to the same orthodontic wire,
all connecting bases are configured to be connected to each respective tooth connector by a common vertical engagement.

9. An orthodontic assembly comprising
a tooth connector configured to be attached onto a tooth to be treated in a patient's dental arch,
a connecting base and a orthodontic working wire arch, wherein the connecting base includes a hollow cavity extending into one face of the connecting base configured to be facing the connector and includes a vertical groove opening into the cavity,
the connecting base is configured to be connected through the vertical groove to the tooth connector by vertical engagement,
the connecting base including a boss retainer constituting an undercut for the vertical engagement to hold the connecting base firmly to the tooth connector,
the connecting base is movable with respect to the orthodontic working wire arch and,
the connecting base is connected to the orthodontic working wire arch by elastically deformable connectors, said elastically deformable connectors configured to generate forces transmitted to the teeth to achieve displacement between a first spatial configuration toward a second spatial configuration,
wherein the working wire arch is rigid, and retains its shape in reaction to the force exerted, and prevents parasitic forces from being transmitted to adjacent teeth, wherein the orthodontic working wire arch also includes a cavity designed to receive all or part of the connecting base.

10. An orthodontic assembly comprising
a tooth connector configured to be attached onto a tooth to be treated in a patient's dental arch, wherein the tooth connector has lateral faces that includes a sunken groove,
a connecting base and a orthodontic working wire arch, wherein
the connecting base includes a hollow cavity extending into one face of the connecting base configured to be facing the connector, and the hollow cavity has a protuberance extending belt-wise over part of a periphery of the cavity, the protuberance being in relief from at least one lateral face of the cavity towards the inside thereof and designed to be received in the sunken groove of the connector,
the connecting base includes a vertical groove opening into the cavity,
the connecting base is configured to be connected through the vertical groove to the tooth connector by a vertical engagement,
the connecting base includes a boss retainer constituting an undercut for the vertical engagement to hold the connecting base firmly to the tooth connector,
the connecting base is movable with respect to the orthodontic working wire arch and,
the connecting base is connected to the orthodontic working wire arch by elastically deformable connectors configured to generate forces transmitted to the teeth to achieve displacement between a first spatial configuration toward a second spatial configuration, wherein the working wire arch is rigid, and retains its shape in reaction to the force exerted, and prevents parasitic forces from being transmitted to adjacent teeth, wherein the orthodontic working wire arch also includes a cavity designed to receive all or part of the connecting base.

11. An orthodontic assembly comprising a tooth connector configured to be attached onto a tooth to be treated in a patient's dental arch, wherein the tooth connector has lateral faces that includes a bead, a connecting base and a orthodontic working wire arch, wherein the connecting base includes a hollow cavity extending into one face of the connecting base designed to be facing the connector, and the hollow cavity has a depression extending belt-wise over part of a periphery of the cavity, the protuberance being in depression from at least one lateral face of the cavity towards the inside thereof and designed to receive the bead in relief, the connecting base includes a vertical groove opening into the cavity, the connecting base is configured to be connected through the vertical groove to the tooth connector by a vertical engagement, the connecting base includes a boss retainer constituting an undercut for the vertical engagement to hold the connecting base firmly to the tooth connector, the connecting base is movable with respect to the orthodontic working wire arch and, the connecting base is connected to the orthodontic working wire arch by elastically deformable connectors configured to generate forces transmitted to the teeth to achieve displacement between a first spatial configuration toward a second spatial configuration, wherein the working wire arch is rigid, and retains its shape in reaction to the force exerted, and prevents parasitic forces from being transmitted to adjacent teeth, wherein the orthodontic working wire arch also includes a cavity designed to receive all or part of the connecting base.

\* \* \* \* \*